United States Patent
Daley

Patent Number: 5,390,681
Date of Patent: Feb. 21, 1995

[54] PROPHYLACTIC DEVICE FOR ORAL SEX

[76] Inventor: Todd C. Daley, P.O. Box 1116, Stafford, Va. 22554

[21] Appl. No.: 143,147

[22] Filed: Oct. 29, 1993

[51] Int. Cl.⁶ .............................. A61F 6/02; A61F 6/04
[52] U.S. Cl. ..................................... 128/842; 128/844; 128/918
[58] Field of Search .............. 128/842, 860, 844, 857, 128/918, 830–841; 604/330, 347–353

[56] References Cited

U.S. PATENT DOCUMENTS

| | | | |
|---|---|---|---|
| 1,219,496 | 3/1917 | Shaulis | 128/834 |
| 1,365,684 | 1/1921 | Guise | 128/860 |
| 1,819,549 | 8/1931 | Fiessler | 128/834 |
| 1,986,988 | 1/1935 | Treadwell | 128/857 |
| 2,358,484 | 9/1944 | Torjussen | 128/857 |
| 2,867,212 | 1/1959 | Nunn | 128/848 |
| 3,905,372 | 9/1975 | Denkinger | 128/834 |
| 4,828,491 | 5/1989 | Gray | 433/136 |
| 4,949,731 | 8/1990 | Harding | 128/848 |

FOREIGN PATENT DOCUMENTS 0025867 12/1936 Australia ............................ 128/837

Primary Examiner—Michael A. Brown

[57] ABSTRACT

A prophylactic device for oral sex comprising a body portion with a reservoir extending from one side and peripheral portion extending from an opposite side thereof.

12 Claims, 2 Drawing Sheets

PROPHYLACTIC DEVICE FOR ORAL SEX

FIELD OF THE INVENTION

This invention relates to a device for preventing the transmission of disease during oral sex. Specifically, the device is used orally by one person who is sexually interacting with the body of another person.

BACKGROUND OF THE INVENTION

Presently, their is a high demand for prophylactic devices to prevent the spread of sexually transmitted diseases. Condoms have been available for centuries, however, only latex type condoms appear to be effective for preventing the transmission of disease during normal heterosexual intercourse.

Conventional condoms are unsuitable for use during oral sex typically involving the use of the tongue of one person on the body of another person, since conventional condoms will not readily fit correctly or stay in place when covering a moving tongue. In response to public demand, oral condoms have been conceived and developed, however, most are difficult or uncomfortable to use. Further, restraining means such as straps or adhesives substantially psychological interfere with person's using such devices.

SUMMARY OF THE INVENTION

The present invention is directed to a device for preventing the transmission of disease by oral sex. Accordingly, an object of the present invention is to provide an effective device to prevent the transmission of disease by oral sex.

Another object of the present invention is to provide a prophylactic device that is easy to use and suitable for performing oral sex.

A further object of the present invention is to provide a prophylactic device that is configured for accommodating the tongue of one person during oral sex, particularly during cunnilingus.

The present invention concerns a prophylactic device termed the "vaginal dish" by the inventor. The device is held by the fingers of the person using the device in front of the person's mouth to allow the person's tongue to interact with the device. Specifically, the tongue is applied and received within a reservoir portion of the device during use.

The vaginal dish in a preferred embodiment comprises an oval-shaped body portion with an oval-shaped reservoir portion centered and extending from one side thereof. The oval-shaped body portion is planar, however, in other embodiments it can be curved in cross-sectional shape. The oval-shaped body portion is provided with an oval-shaped peripheral rim portion extending from an opposite side thereof. The oval-shaped peripheral rim portion is provided with an oval-shaped bead portion. The major axis of the oval-shaped reservoir portion is set perpendicular relative to the major axis of the oval-shaped body portion.

In the preferred embodiment, the reservoir portion, body portion, rim portion, and bead portion are all oval-shaped, however, other shapes such as circular or other curved shapes can be selected to provide suitable embodiments of the present invention. Further, the individual portions may vary in shape from each other (e.g. oval-shaped pouch portion and circular shaped body portion, circular shaped rim portion, and circular shaped bead portion). The oval-shaped peripheral rim portion is utilized as a gripping portion for a person using the device. Specifically, the person places the tip of their index finger and thumb of each hand inside the oval-shaped peripheral rim portion, and extends the index finger apart from the thumb of each hand while pulling their hands apart to stretch the body portion. The peripheral rim portion securely receives the index finger tip and thumb tip of each hand preventing them from slipping out of the peripheral rim during use thereof.

In this configuration, the person using the device places the device in front of their mouth and presses their tongue into the pouch portion while placing the pouch portion in contact with another person during use.

DETAILED DESCRIPTION OF PREFERRED EMBODIMENTS

Figure 1:
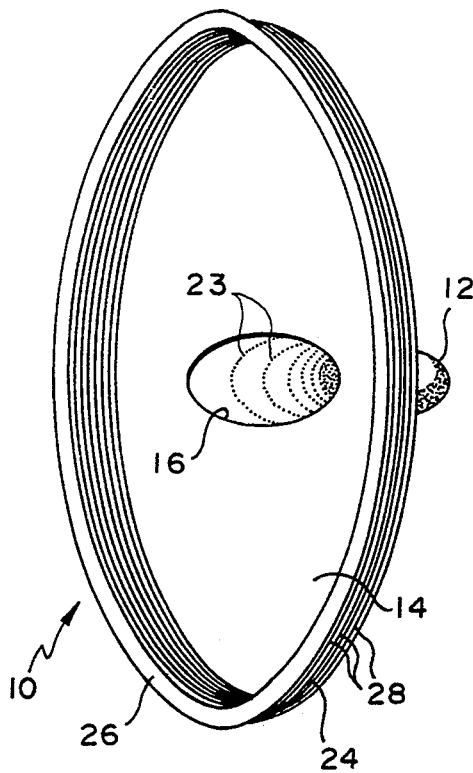
FIG. 1 is a perspective view of a preferred embodiment according to the present invention.
Figure 2:
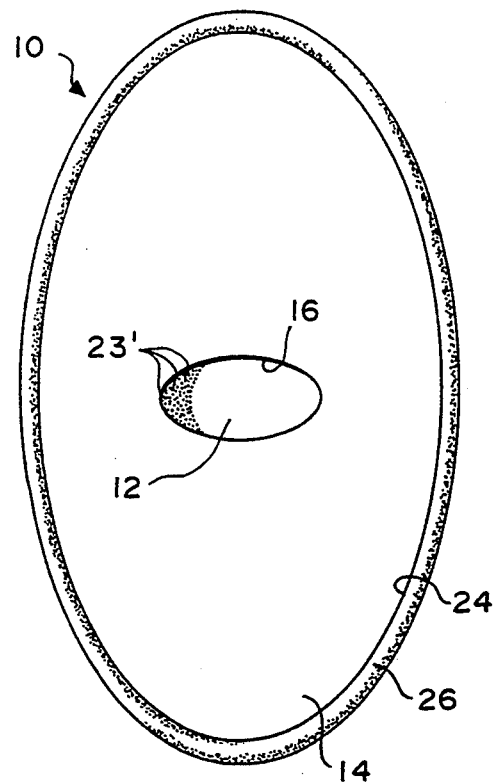
FIG. 2 is an elevational view of one side of a preferred embodiment of the device according to the present invention.
Figure 3:
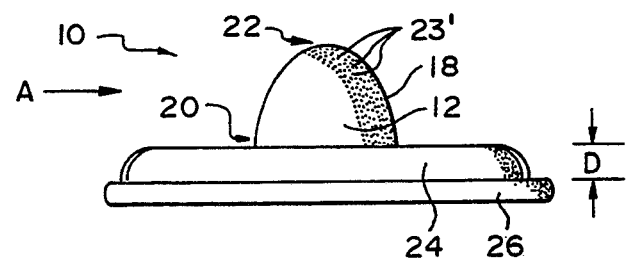
FIG. 3 is an edge view of the device shown in FIG. 1.

A preferred embodiment of a device 10 according to the present invention is shown in FIGS. 1-3.

The device 10 comprises an oval-shaped reservoir portion 12 extending from one side of an oval-shaped body portion 14. Specifically, the base of the reservoir portion 12 is oval-shaped and defines an oval-shaped opening 16 through the body portion 14 entering into the reservoir portion 12. Further, a side profile 18 of the reservoir portion 12, as shown in FIG. 3, is also oval shaped and tapers from the base 20 to the tip 22. The reservoir portion 12 is also oval-shaped when viewing the profile of the pouch portion 12 in direction A as seen in FIG. 3. Thus, the reservoir portion 12 is of a double tapered configuration.

The reservoir portion 12 is most desirably oval-shaped and double tapered in the configuration illustrated in the drawings to accommodate a person's tongue or finger(s), which is more or less oval in cross-sectional shape and having a double tapered configuration. This oval-shaped double tapered configuration closely conforms to the outer surface of the tongue and provides maximum sensitivity to a user since the material of the tongue portion is not substantially stretched against the surface of the tongue.

However, since the device 10 is preferably made of latex rubber or other suitable natural or synthetic rubber and plastic type materials, the reservoir portion 12 can be made to have other suitable curved shapes such as hemispherical, and can conform to a person's tongue when is use.

The reservoir portion 12 can be optionally provided with sensitivity enhancing projections such as circumferential ridges 23 as shown in FIG. 1, or nodules 23' as shown in FIG. 3.

Further, the reservoir portion 12 is desirably centered in the body portion 14 due to the manner of use to be explained in detail below. However, the reservoir portion 12 can be off-centered for certain applications.

The body portion 14 is provided with an oval-shaped peripheral rim portion 24 having an oval-shaped bead portion 26. An inner surface of the peripheral rim portion 24 provides a gripping portion for the tips of a person's index finger and thumb of each hand during use. In a preferred embodiment, at least an inner surface of the peripheral rim is provided with plural ridges 28 to further provide gripping action with the tip of the person's index finger and thumb of each hand during use.

The peripheral rim portion 24 has a width D, as shown in FIG. 3. The peripheral bead portion 26 is desirably set off a predetermined distance from the body portion 14 up to a distance equal to the width D. The width D is substantially less than the width of the body portion 14 defining a plate-like overall configuration. Further, this arrangement provides a secure gripping arrangement for the tips of the fingers and thumbs during use as explained in detail below.

Figure 4:
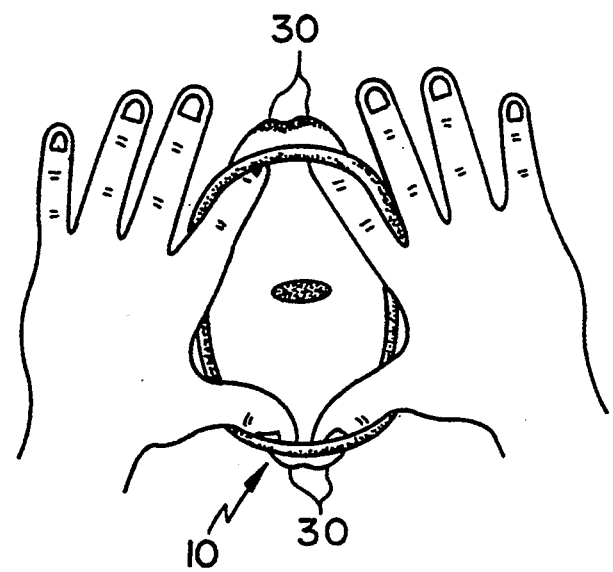
FIG. 4 illustrates gripping the device with the tips of the index finger and thumb of each hand of a user.
Figure 5:
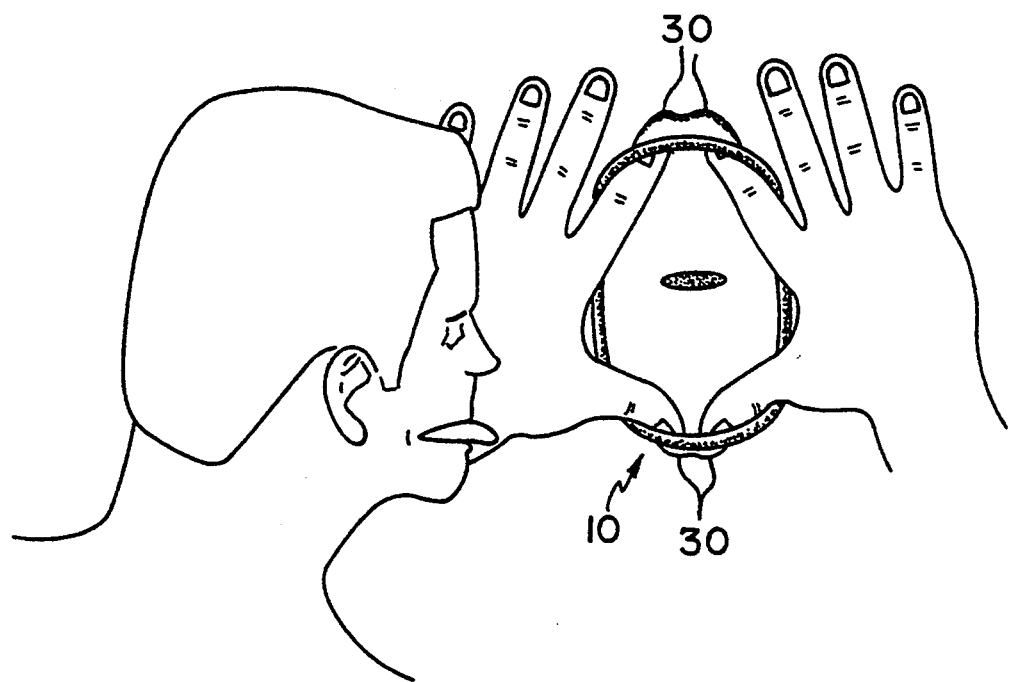
FIG. 5 illustrates the relationship between the gripped device and a person using the device.

One edge of the peripheral rim portion 24 is connected to the body portion 14, and an opposite edge of the peripheral rim portion 24 is connected to the peripheral bead portion 26. The bead portion 26 retains the tips of a person's index finger and thumb of each hand inside the peripheral rim 24 during use, as shown in FIGS. 4 and 5. Further, the peripheral bead portion 26 has a greater tensile strength than the peripheral rim portion 24. For example, the peripheral bead portion 26 can be made of the same material as the peripheral rim portion 24 but rolled up providing a bead of multiple layers of the same material providing a substantially stronger component under tensile force. Alternatively, the peripheral bead portion 26 is formed to be thicker than the peripheral rim portion 24.

During use, the user spreads apart the peripheral rim portion 24 and the peripheral rim portion 24 resiliently yields outwardly defining gripping points 30 on the inside of the peripheral rim portion 24 while the bead portion 26 having a greater tensile strength yields to a lesser degree. This arrangement retains the tips of the fingers and thumbs behind the bead portion 26 further enhancing the degree of gripping by the tips of the fingers and thumbs.

I claim:

1. A prophylactic device for oral sex, comprising:
    a substantially flat plate body portion made of a thin flexible polymer material, said flat plate body portion having a peripheral edge of predetermined dimensions;
    a tongue shaped reservoir portion extending substantially perpendicularly from one side of said flat plate body portion, said reservoir portion having an entrance opening on an opposite side of said flat plate body portion that is substantially smaller than the dimensions of said peripheral edge of said flat plate body portion and positioned inside said peripheral edge of said flat plate body portion;
    a peripheral rim portion having a predetermined width and extending from said peripheral edge of said flat plate body portion on an opposite side of said body portion relative to said reservoir portion, said peripheral rim having a peripheral edge; and
    a bead portion provided on said peripheral rim portion, said bead portion is set off a predetermined distance from said flat plate body portion by said peripheral rim portion, whereby a user places their fingertips inside said peripheral rim and forces their fingertips outwardly causing said peripheral rim to expand outwardly while said bead portion substantially maintains its diameter and prevents the user's finger tips from slipping outwardly and losing grip of the device.

2. A device according to claim 1, wherein said reservoir portion has an oval-shaped cross-section and is double tapered.

3. A device according to claim 1, wherein said body portion is planar.

4. A device according to claim 1, wherein said peripheral rim is provided with a plurality of ribs on an inner surface thereof.

5. A device according to claim 1, wherein said bead portion has a greater tensile strength than said peripheral rim portion to enhance gripping of the device.

6. A device according to claim 1, wherein said reservoir has an oval-shaped opening through said body portion and said body portion is oval-shaped.

7. A device according to claim 6, wherein said oval-shaped opening has a major axis set perpendicular to a major axis of said oval-shaped body portion.

8. A device according to claim 1, wherein said reservoir portion is provided with plural sensitivity enhancing projections.

9. A device according to claim 1, wherein said projections are circumferential ridges.

10. A prophylactic device for oral sex, comprising:
    a substantially flat disk body portion made of a thin flexible polymer, and having a peripheral rim;
    a tongue shaped reservoir portion extending from said flat disk body portion, said reservoir portion positioned a predetermined distance inside said peripheral edge of said flat disk body portion;
    a peripheral rim having a predetermined width, said peripheral rim extending from said peripheral edge of said flat disk body portion to a peripheral edge set off a distance from said flat disk body portion, said peripheral rim extending from an opposite side of said flat disk body portion relative to said tongue shaped reservoir portion; and
    a bead portion provided at said peripheral edge of said flat disk body portion.

11. A device according to claim 10, wherein said peripheral rim extends from said peripheral edge of said flat disk body portion in a continuous manner.

12. A device according to claim 11, wherein said peripheral rim is defined with a curved transition portion extending from said flat disk body portion to a cylindrical portion of said peripheral rim.

* * * * *